(12) United States Patent
Zhu et al.

(10) Patent No.: US 8,995,609 B2
(45) Date of Patent: Mar. 31, 2015

(54) X-RAY COMPTON SCATTER IMAGING ON VOLUMETRIC CT SYSTEMS

(75) Inventors: Lei Zhu, Roswell, GA (US); Tianye Niu, Atlanta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 265 days.

(21) Appl. No.: 13/565,337

(22) Filed: Aug. 2, 2012

(65) Prior Publication Data

US 2013/0032715 A1 Feb. 7, 2013

Related U.S. Application Data

(60) Provisional application No. 61/514,246, filed on Aug. 2, 2011.

(51) Int. Cl.

| | |
|---|---|
| *A61B 6/00* | (2006.01) |
| *G01N 23/04* | (2006.01) |
| *G21K 1/02* | (2006.01) |
| *A61B 6/03* | (2006.01) |

(52) U.S. Cl.
CPC ............... *G01N 23/046* (2013.01); *G21K 1/02* (2013.01); *A61B 6/032* (2013.01); *A61B 6/4078* (2013.01); *A61B 6/4233* (2013.01); *A61B 6/483* (2013.01); *G21K 2207/005* (2013.01); *A61B 6/508* (2013.01); *G01N 2223/419* (2013.01); *G01N 2223/612* (2013.01)
USPC ............................................................. 378/6

(58) Field of Classification Search
CPC . G21K 1/02; G21K 2207/005; G01N 23/046; A61B 6/032; A61B 6/4233; A61B 6/4078

USPC ................................ 378/4–21, 145, 147, 149
See application file for complete search history.

(56) References Cited

U.S. PATENT DOCUMENTS

| | | | |
|---|---|---|---|
| RE37,899 E * | 11/2002 | Grodzins et al. ................ | 378/86 |
| 2001/0056234 A1 | 12/2001 | Weinberg | |

OTHER PUBLICATIONS

Peterson, Todd E. et al., "A Prototype Low-Energy, Multi-pinhole SPECT System for Small-Animal Imaging", Nuclear Science Symposium Conference Record, pp. 2999-3002, Oct. 2004.

* cited by examiner

*Primary Examiner* — Courtney Thomas
(74) *Attorney, Agent, or Firm* — Troutman Sanders LLP; Ryan A. Schneider; Andrew C. Doherty

(57) ABSTRACT

Briefly described, in an exemplary form, the present invention discloses a system, method and apparatus for X-ray Compton scatter imaging. In one exemplary embodiment, the present invention uses two detectors in a volumetric CT system. A first detector is positioned generally in-line with the angle of attack of the incoming energy, or, generally in-line of path x, where x is the path of the incoming energy. The first, or primary, detector detects various forms of radiation emanating from an object undergoing testing. In some embodiments, the present invention further comprises a Compton scattering system positioned generally normal to path x. In some embodiments, the Compton scattering subsystem comprises a second detector and a pin-hole collimator. The second detector detects Compton scattering energy from the object being tested.

22 Claims, 6 Drawing Sheets

X-RAY COMPTON SCATTER IMAGING ON VOLUMETRIC CT SYSTEMS

CROSS REFERENCE TO RELATED APPLICATION

This application claims benefit of U.S. Provisional Patent Application Ser. No. 61/514,246 filed 2 Aug. 2011, entitled, "X-Ray Compton Scatter Imaging on Volumetric CT Systems," which application is hereby incorporated fully by reference.

BACKGROUND OF THE INVENTION

1. Field of the Invention

The present invention relates generally to X-Ray Compton scatter imaging.

2. Description of the Related Art

Through the advancement of computing systems, conventional medical and industrial imaging systems provide an increased level of information available to the researcher. X-ray computed tomography can be used for medical imaging and industrial imaging methods employing tomography created by computer processing. A computed tomography (CT) scan can produce a large amount of data that can be manipulated, through a process known as "windowing", in order to demonstrate various bodily structures based on their ability to block the X-ray beam. These CT methods, also called computed axial tomography scan (CAT scan), use digital geometry processing to generate a three-dimensional image of the inside of an object from a large series of two-dimensional X-ray images, typically taken around a single axis of rotation.

Medical researchers have used CT to supplement X-ray and ultrasonic imaging. Because of its ability to detect various types of bodily tissue, the use of CT in preventative measures has increased. For example, CT is increasingly being used to screen for various types of diseases such as cancer and conditions such as heart disease. There are several advantages that CT has over traditional 2D medical radiography. First, CT can eliminate the superimposition of images of structures outside the area of interest. Second, because of the inherent high-contrast resolution of CT, differences between tissues that differ in physical density by less than 1% can be distinguished. Finally, data from a single CT imaging procedure consisting of either multiple contiguous or one helical scan can be viewed as images in the axial, coronal, or sagittal planes, depending on the diagnostic task. This is referred to as multiplanar reformatted imaging.

Although the availability and usage of CT has increased dramatically over the last two decades, the increased use of X-rays has caused some concern. Although the data and results are not conclusive, it is estimated that 0.4% of current cancers in the United States are due to CTs. CT scans involve the use of 10 to 100 times more ionizing radiation than typical X-rays. Estimated lifetime cancer mortality risks attributable to the radiation exposure from a CT in a 1-year-old are 0.18% (abdominal) and 0.07% (head)—an order of magnitude higher than for adults—although those figures still represent a small increase in cancer mortality over the background rate.

In the diagnostic energy range (20-140 keV), photons interact with matters via three fundamental mechanisms: photoelectric absorption, coherent scattering and Compton scattering. To maximize dose efficiency, i.e. amount of information per dose, an ideal x-ray diagnostic imaging system should utilize all the useful information from the interactions between x-ray photons and the object, including photoelectric absorption, coherent scattering and Compton scattering. Conventional x-ray CT imaging obtains the total linear attenuation coefficients from the three mechanisms mentioned above, and therefore does not provide an effective amount of patient information per dose.

Many techniques have been proposed to acquire images from each of the three mechanisms. For example, photoelectric response has been used to track the nano-particles injected into human bodies for cancer therapy. Phase-contrast imaging measures coherent scatter signals and significantly increases image contrasts as compared to conventional CT imaging. Compton scatter imaging exhibits many merits over conventional CT imaging as well. It provides accurate electron density distributions, which lays a solid foundation for precise radiation dose calculation in both diagnostic and therapeutic energy ranges.

Compton scattering is a type of inelastic scattering that X-rays and gamma rays (both photons with different energy ranges) undergo in matter. The inelastic scattering of photons in matter results in a decrease in energy (increase in wavelength) of an X-ray or gamma ray photon, called the Compton Effect. Part of the energy of the X/gamma ray is transferred to a scattering electron, which recoils and is ejected from its atom (which becomes ionized), and the rest of the energy is taken by the scattered, "degraded" photon. The amount the wavelength changes by is called the Compton shift.

Compton scatter images can also be combined with the conventional CT images for contrast enhancement and material decomposition. Systems specialized for Compton scatter imaging have been designed since the early days of CT. Based on the targeting methods of scatter sources, the data acquisition modes of these systems can be divided into two categories. The first group targets the scatter sources point-by-point by moving a diverging-hole collimator and the detector together. This relative movement can severely degrade data acquisition efficiency. The second type of method traces the multiple sources of measured scatter photons using their energy information. These methods require an energy-sensitive detector, which is expensive using the current manufacturing technologies and is not available on commercial volumetric CT (VCT) systems. Thus, conventional Compton imaging systems are either inefficient on dose and imaging time or require an energy-selective detector.

BRIEF SUMMARY OF THE INVENTION

Briefly described, in an exemplary form, the present invention discloses a system, method and apparatus for X-ray Compton scatter imaging. In one exemplary embodiment, the present invention uses two detectors in a volumetric CT system. A first detector is positioned generally in-line with the angle of attack of the incoming energy, or, generally in-line of path x, where x is the path of the incoming energy. The first, or primary, detector detects various forms of radiation emanating from an object undergoing testing. In some embodiments, the present invention further comprises a Compton scattering system positioned generally normal to path x. In some embodiments, the Compton scattering subsystem comprises a second detector and a pin-hole collimator. The second detector detects Compton scattering energy from the object being tested.

In one exemplary embodiment, the present invention is an energy computed tomography system comprising an energy source for directing energy along at least a path x toward an object located a distance from the energy source, wherein a portion of the energy undergoes Compton effect upon interaction with the object to create a plurality of Compton scatter photons, a first detector positioned a first distance from the object generally in-line of path x for detecting one or more types of radiation, and a Compton scattering subsystem located a second distance from the object generally normal to path x. In some embodiments, the Compton scattering subsystem comprises a second detector and a pin-hole collimator having at least one pin-hole, the stationary pin-hole collimator located between the object and the second detector, wherein Compton scattering is measured for lower energy passing through the at least one pin-hole collimator measured by the second detector and wherein the system provides data related to interior features within the object.

In some embodiments, the energy source is selected from a group consisting of an X-ray or gamma ray source.

In some embodiments, the object is a human or a part of a human.

In some embodiments, first detector is stationary or is moved during data acquisition.

In some embodiments, the second detector is stationary during a test or is moved during data acquisition.

In some embodiments, the pin-hole collimator is stationary during a test or is moved during data acquisition.

In some embodiments, the side detector is placed less than approximately 50 degrees from normal to path x.

Another embodiment of the present invention is a method of computed tomography imaging, the comprising providing an energy source for directing energy along at least a path x toward an object located a distance from the energy source, wherein a portion of the energy undergoes Compton effect upon interaction with the object to create a plurality of Compton scatter photons, positioning a first detector a first distance from the object generally in-line of path x for detecting one or more types of radiation, and positioning a Compton scattering subsystem a second distance from the object generally normal to path x. In some embodiments, the Compton scattering subsystem comprises a second detector and a pin-hole collimator having at least one pin-hole, the stationary pin-hole collimator located between the object and the second detector, wherein Compton scattering is measured for lower energy passing through the at least one pin-hole collimator measured by the second detector, wherein the system provides data related to interior features within the object, and initializing the energy source to commence imaging.

In another embodiment, the present invention is an energy computed tomography system, comprising an energy source for directing energy along at least a path x toward an object located a distance from the energy source, wherein a portion of the energy undergoes Compton effect upon interaction with the object to create a plurality of Compton scatter photons, a first detector positioned a first distance from the object generally in-line of path x for detecting one or more types of radiation, a Compton scattering subsystem located a second distance from the object generally normal to path x, the Compton scattering subsystem comprising, a second detector; and a collimator located between the object and the second detector, wherein Compton scattering is measured for lower energy passing through the collimator measured by the second detector, and wherein the system provides data related to interior features within the object. In an alternative of this embodiment, the collimator is selected from the group consisting of a pin-hole collimator and a parallel-slit collimator. In a still further alternative of this embodiment, the energy source is selected from the group consisting of X-ray and proton.

These and other objects, features, and advantages of the present invention will become more apparent upon reading the following specification in conjunction with the accompanying drawing figures.

DETAILED DESCRIPTION OF PREFERRED EMBODIMENTS

Figure 1:
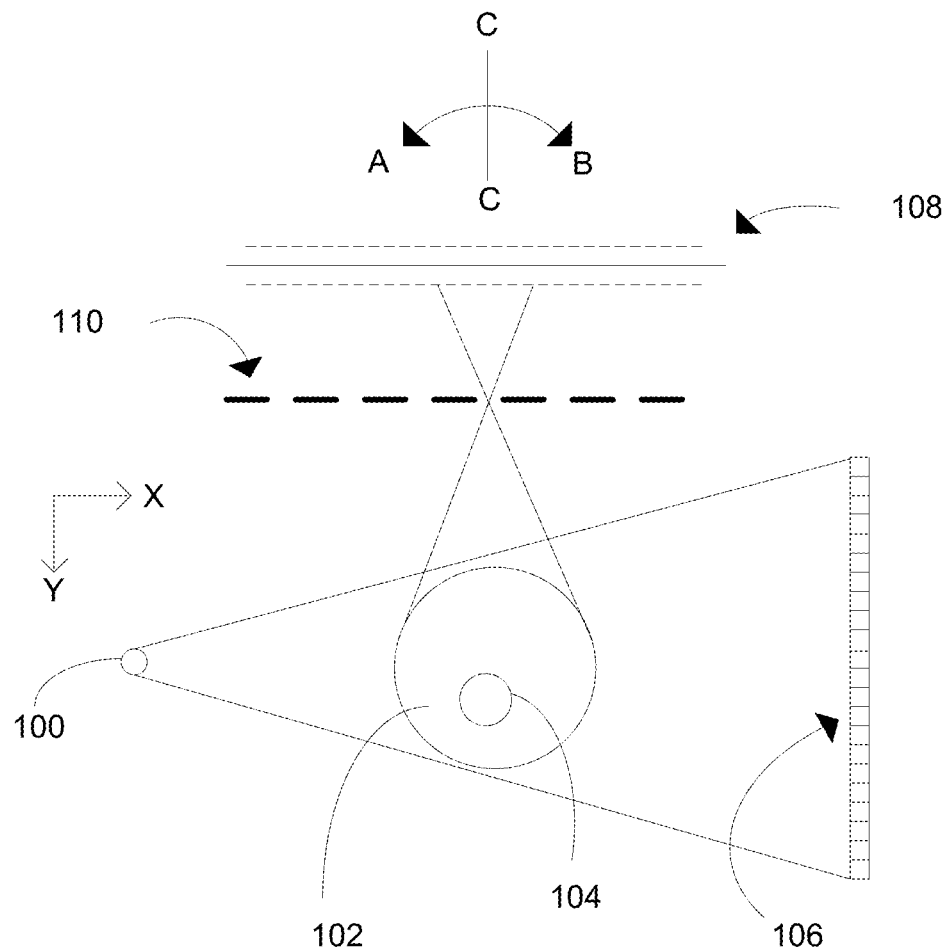
FIG. 1 is an illustration of an exemplary X-ray Compton scattering imaging system, according to an exemplary embodiment of the present invention.

Although preferred embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Various embodiments of the present invention are directed to an x-ray imaging system that maximizes dose efficiency and utilizes as much of the useful information from the interaction process between x-ray photons and the object. An embodiment of the present invention uses a Compton scatter imaging method, system and apparatus to measure electron densities of the object based on photon attenuation and Compton scatter probability. Various embodiments of the present invention are designed using a clinical cone-beam CT system. Other embodiments of the present invention use various types of radiation beams such as proton radiation. The present invention is not limited to any one specific type of radiation and may include other types of radiation.

In one embodiment of the present invention, a pinhole collimator is placed in front of a side detector. The incident direction of each measured scatter signal can be determined if single scattering is assumed. As compared to various conventional methods, the present invention can be a simpler and more efficient data acquisition process. Therefore, the present invention can be more practical and widely applicable on clinical CT systems with a conventional large-area detector. Various embodiments of the present invention can be used with conventional CT systems. Further, various embodiments of the present invention can use other types of collimators, as the present invention is not limited to the use of a pin-hole collimator. For example, a parallel slit collimator can be used which can increase the photon detection efficiency over a pin-hole collimator, but can suffer from a larger scatter photon localization error.

In addition to a primary, or "front", detector, placed in line with a target in conventional CT systems, various embodiments of the present invention use a secondary, or "side" detector, in an orientation relative to the front detector. A pinhole collimator is placed in between the target and the secondary detector. In some embodiments, the collimator has sparsely distributed pinholes such that the incident direction of each scatter signal can be measured on the detector and can be determined from the system geometry. Some embodiments of the present invention acquire both conventional CT projection data and scatter data in a single scan, thereby maximizing the use of a single radiation event.

FIG. 1 is an illustration of an X-ray Compton scatter imaging system according to one embodiment of the present invention. As shown in FIG. 1, X-rays emanate from focal point 100 to radiate object 102. Object 102 may be a human body or a portion of a body, such as a leg or chest cavity, or can be a non-human object. The system of FIG. 1 can be used to image structure 104 of object 102. In some examples, structure 104 can be a potentially cancerous cellular structure within object 102.

Front detector 106 receives the radiation transmitted or deflected by object 102 or structure 104 in a generally "x" direction from focal point 100, or the X-ray source. Because of its location in relation to focal point 100, typically, front detector 106 will be relatively heavily shielded. If front detector 106 was not shielded, front detector 106 can receive radiation directly from focal point 100, thus saturating front detector 106.

The system of FIG. 1 further comprises side detector 108. Side detector 108 can have a construction similar to front detector 106 or can be constructed (optimized) to detect specific types of radiation, such as Compton scattering. Side detector 108 is used to detect additional photons not detected by front detector 106 because of the location of front detector 106 in relation to object 102. When irradiated by a source, object 102 or structure 104 will radiate or reflect various types of radiation in various directions. To locate the source of scatters photons, pinhole collimator 110 is placed in between side detector 108 and object 102. In some configurations, side detector 108 is placed in a generally 90 degree orientation, or in the "y" direction, to front detector 106 to remove or reduce the influence from other scatter sources (e.g. coherent scatter) so that, preferably, the majority of the received scatter photons on side detector 108 are generated by Compton scattering processes.

The measured scatter signal intensity on side detector 108 from a single scatter source, such as object 102 or structure 104, can be described as (assuming no multiple scattering) Equation (1):

$$I_s(E, \theta) = I_0 e^{-\int \mu_p dl} \cdot \frac{d\sigma}{d\Omega}(E, \theta) \cdot \rho_e \cdot e^{-\int \mu_s dl} \cdot \Delta\Omega = C(E, \theta) \cdot \rho_e \quad (1)$$

where $I_s$ is the measured scatter intensity on detector, $I_o$ is the intensity of the X-ray source, $\mu_p$ and $\mu_s$ are the linear attenuation coefficients of the object along the paths of the primary photons and scatter photons, respectively, E is the incident X-ray energy, $\Theta$ is the scatter angle, $$\frac{d\sigma}{d\Omega}(E, \theta)$$

is the Klein-Nishina differential cross section, $\Delta\Omega$ is the solid angle centered at scatter source and spanned by corresponding detector pixel, $\rho_e$ is the electron density of the material at point P and $$C(E, \theta) = I_0 e^{-\int \mu_p dl} \cdot \frac{d\sigma}{d\Omega}(E, \theta) \cdot e^{-\int \mu_s dl} \cdot \Delta\Omega.$$

Equation (1) shows the detected scatter intensity from one scatter source. When a fan-beam or a cone-beam source is used, the intensity on side detector 108 measures the total number of scatter photons along a line passing through detector 108 and collimator 110. Compton scatter images can be obtained using various techniques such as linear programming.

Figure 2:
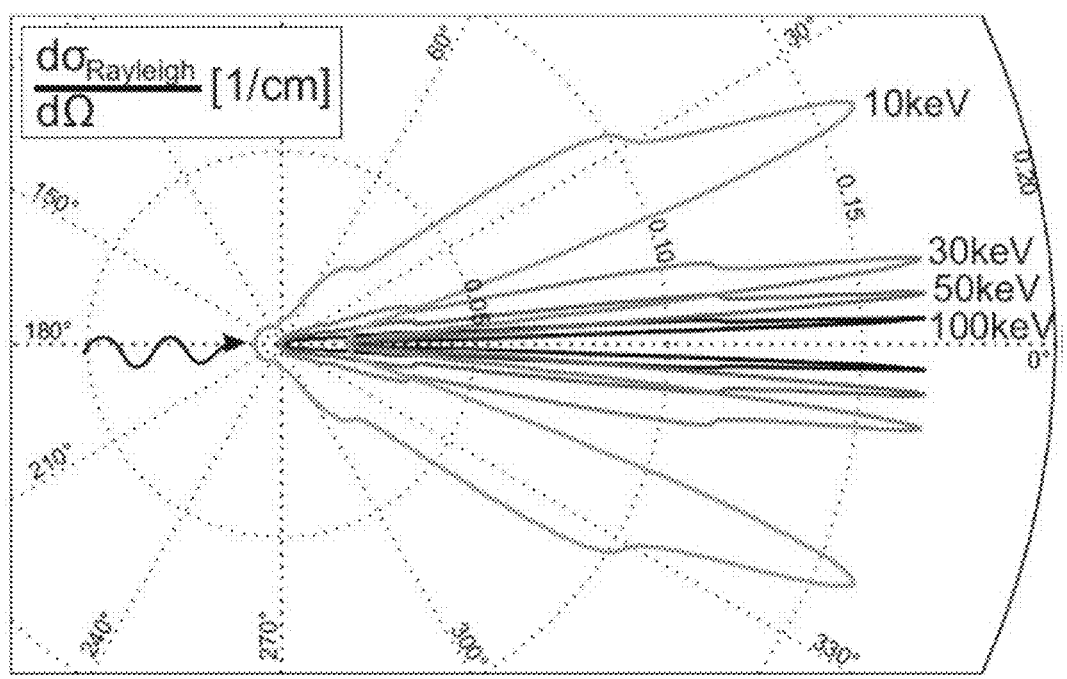
FIG. 2 illustrates the angular distribution of the Rayleigh process.
Figure 3:
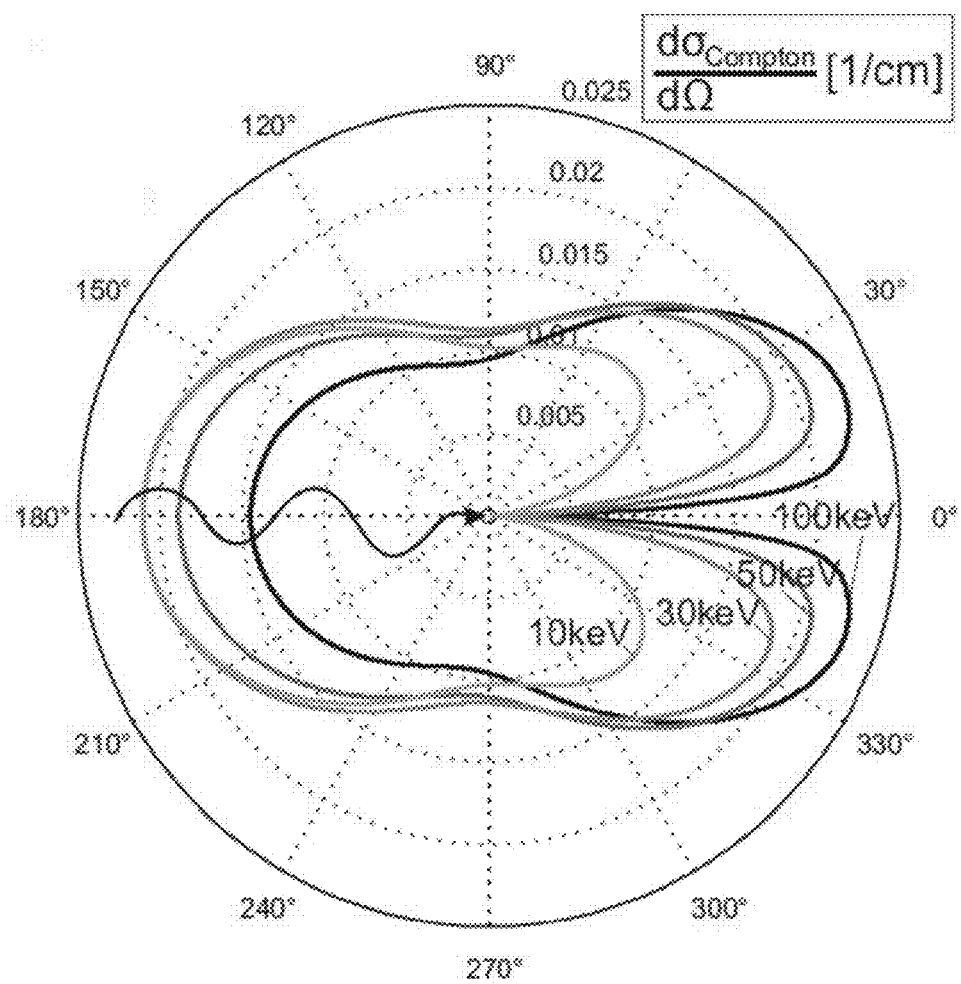
FIG. 3 illustrates the angular distribution of Compton scattering.

As noted above, the position of side detector 108 in relation to source direction and/or front detector 106 is to reduce to the probability that primary and/or Rayleigh scattered photons hit side detector 108. FIG. 2 is a polar diagram of the differential Rayleigh cross sections for water at room temperature as a function of the scattering angle and for various exemplary photon energies. FIG. 3 is a polar diagram of the differential Compton cross sections for water at room temperature as a function of the scattering angle and for various exemplary photon energies. As can be seen, photons from Rayleigh processes distribute well focuses within a narrow angular range (~30 degrees, as shown in FIG. 2), whereas the photons of Compton scattering are more uniformly distributed across the 360 degree range (as shown in FIG. 3). Therefore, in one embodiment of the present invention, side detector 108 of FIG. 1 is placed generally normal to the incident X-ray beam to avoid both primary photons (i.e. the photons coming directly from the X-ray source) and Rayleigh scattered photons.

Returning to FIG. 1, in further embodiments, side detector 108 can be placed at one or more angular displacements in relation to the path of the incoming energy source. This may be done for various reasons including, but not limited to, optimization of Compton scatter detection, compensation for object irregularities, compensation for incoming energy angles of attack, or to obtain additional data. Side detector 108 can be moved in angular rotational direction "A" or direction "B" from normal position "C-C" to an angular displacement less than approximately 50 degrees from normal position "C-C". In some embodiments, side detector 108 is stationary once radiation begins and, in still further embodiments, side detector 108 can be moveable along an angular displacement. In still further embodiments, the distance of side detector 108 from object 102 can be varied. In additional embodiments, the distance of collimator 110 from either side detector 108 or object 102 can also be varied.

Figure 4:
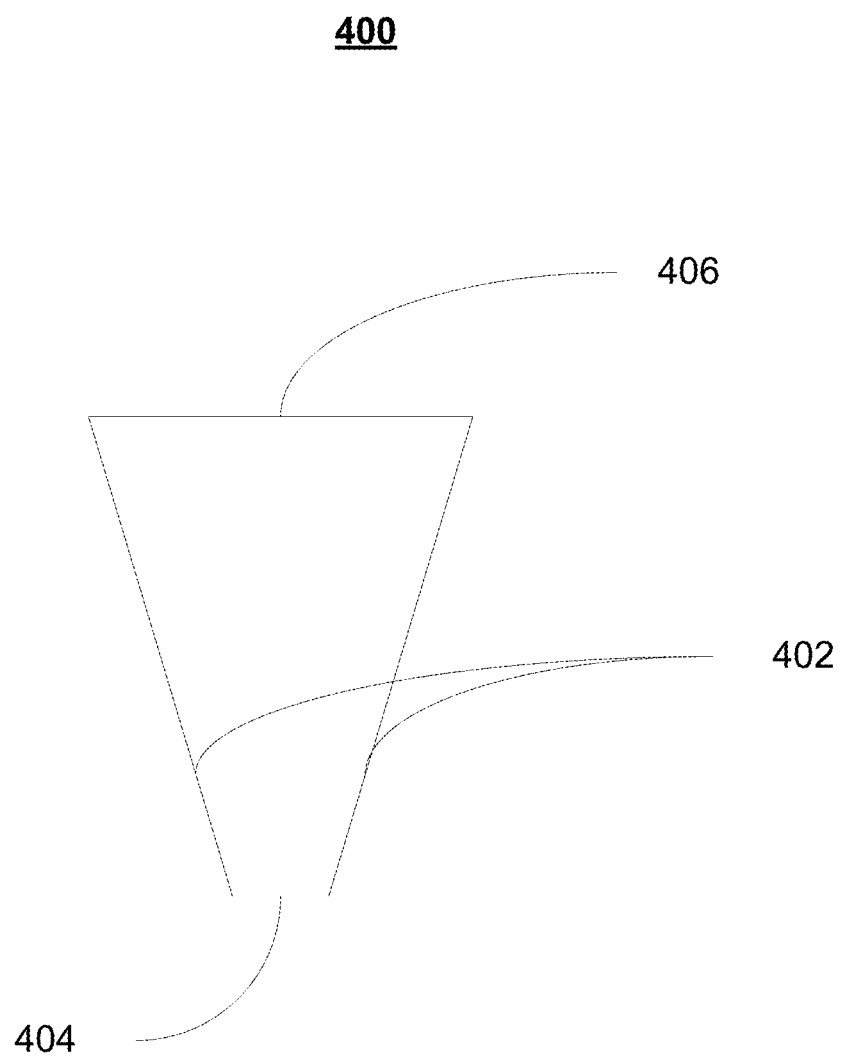
FIG. 4 is an illustration of an exemplary pin-hole detector.
Figure 5:
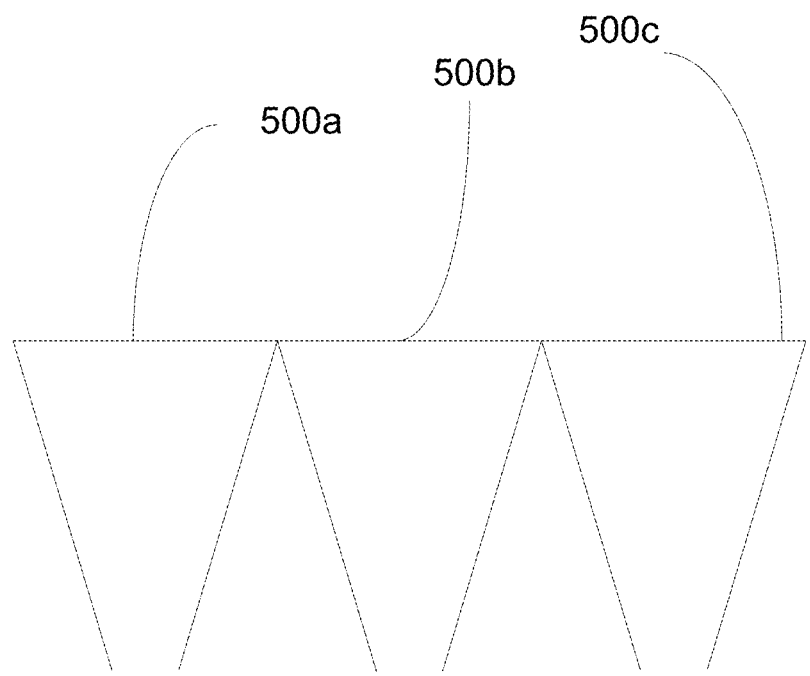
FIG. 5 is an illustration of a portion of a pin-hole collimator that can be used in various embodiments of the present invention.

In order to detect the location of Compton scatter photons from object 102 or structure 104, in some embodiments, a pinhole collimator is used. FIG. 4 is an illustration of a pinhole collimator that may be used. Collimator 400 has a wall 402 which can be conical in shape. The shape of wall 402 defines an opening 404 and back end 406. Opening 404 is positioned so that radiation, such as Compton scattering, enters collimator 400 and can travel to back end 406. In some embodiments, back end 406 is comprised of one or more radiation detectors, such as side detector 108 of FIG. 1. To detect a relatively large area, more than one collimator may be placed in position with each other, as shown in FIG. 5. Pinhole collimators 500*a-c* can be placed next to each other. By using a pinhole collimator, such as collimator 400 of FIG. 4, the source or location of incident radiation from object 102 or structure 104 can be determined to some degree of accuracy.

Figure 6:
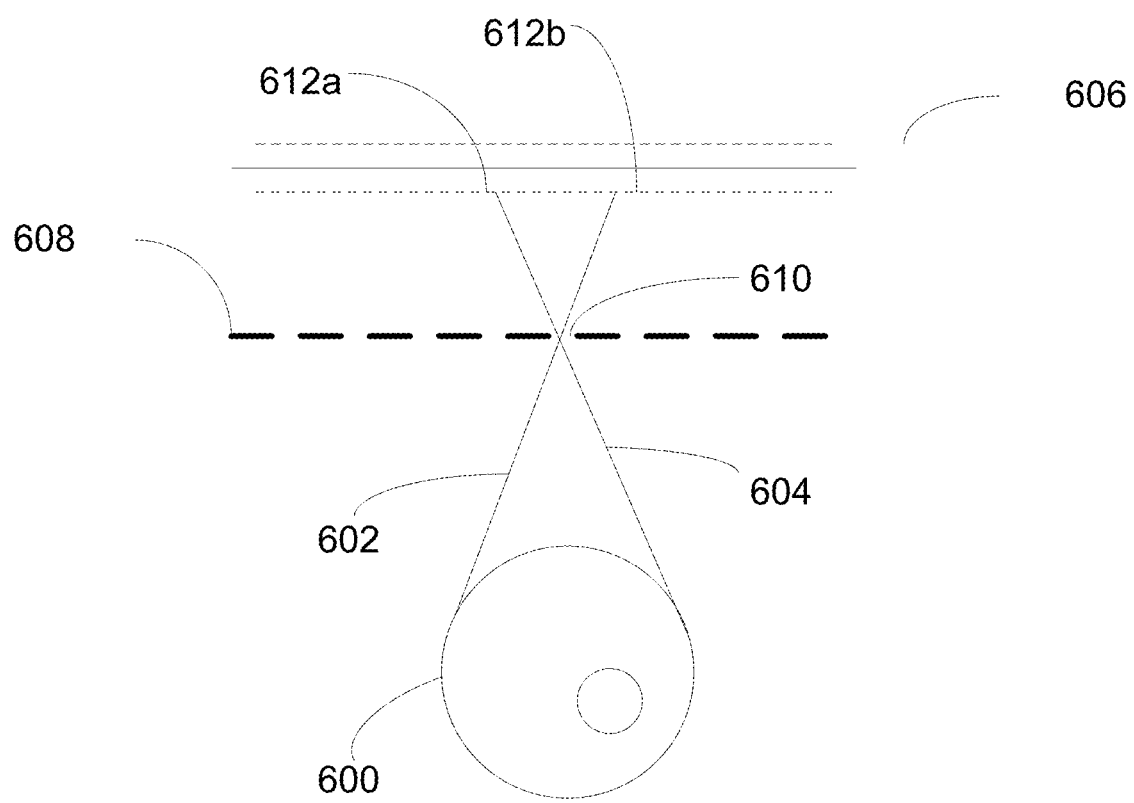
FIG. 6 is an illustration showing an exemplary side detector in accordance with an exemplary embodiment of the present invention.

FIG. 6 illustrates a basic localization principle when using a pinhole collimator. Body 600 has been irradiated by an X-ray source. Compton scatter photons, represented by lines 602 and 604 to show directionality, are radiated from body 600. Side detector 606 is placed in a position to receive photons 602 and 604. Photons 602 and 604 impinge on detector 606 through pinhole collimator 608 aperture 610. Detector 606 crystal detectors 612*a* and 612*b* detect photons 604 and 602. By calculating the locations of collimator 608 aperture 610 in relation to detectors 612*a* and 612*b*, the location of body 600 can be calculated, thus providing not only a determination of the existence of an object, such as body 600, but the location of body 600 can be determined as well.

Numerous characteristics and advantages have been set forth in the foregoing description, together with details of structure and function. While the invention has been disclosed in several forms, it will be apparent to those skilled in the art that many modifications, additions, and deletions, especially in matters of shape, size, and arrangement of parts, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

We claim:

1. An energy computed tomography system, comprising:
   an energy source for directing energy along at least a path x toward an object located a distance from the energy source, wherein a portion of the energy undergoes Compton effect upon interaction with the object to create a plurality of Compton scatter photons;
   a first detector positioned a first distance from the object generally in-line of path x for detecting one or more types of radiation;
   a Compton scattering subsystem located a second distance from the object generally normal to path x, the Compton scattering subsystem comprising:
      a second detector; and
      a pin-hole collimator having at least one pin-hole, the pin-hole collimator located between the object and the second detector;
   wherein Compton scattering is measured for lower energy passing through the at least one pin-hole collimator measured by the second detector; and
   wherein the system provides data related to interior features within the object.

2. The system of claim 1, wherein the energy source is selected from a group consisting of an X-ray or gamma ray source.

3. The system of claim 1, wherein the object is a human or a part of a human.

4. The system of claim 1, wherein the first detector is stationary during data acquisition or the first detector is movable during data acquisition.

5. The system of claim 1, wherein the second detector is stationary during data acquisition or is movable during data acquisition.

6. The system of claim 1, wherein the pin-hole collimator is stationary during data acquisition or is movable during data acquisition.

7. The system of claim 1, wherein the side detector is placed less than approximately 50 degrees from normal to path x.

8. A method of computed tomography imaging, comprising:
   providing an energy source for directing energy along at least a path x toward an object located a distance from the energy source, wherein a portion of the energy undergoes Compton effect upon interaction with the object to create a plurality of Compton scatter photons;
   positioning a first detector a first distance from the object generally in-line of path x for detecting one or more types of radiation;
   positioning a Compton scattering subsystem a second distance from the object generally normal to path x, the Compton scattering subsystem comprising:
      a second detector; and
      a pin-hole collimator having at least one pin-hole, the pin-hole collimator located between the object and the second detector;
   wherein Compton scattering is measured for lower energy passing through the at least one pin-hole collimator measured by the second detector;
   wherein the system provides data related to interior features within the object; and
   initializing the energy source to commence imaging.

9. The method of claim 8, wherein the energy source is selected from a group consisting of an X-ray source and gamma ray source.

10. The method of claim 8, wherein the object is a human or a part of a human.

11. The method of claim 8, wherein first detector is maintained stationary or moved during data acquisition.

12. The method of claim 8, further comprising holding the second detector stationary during data acquisition or moving the secondary detector during data acquisition.

13. The method of claim 8, further comprising holding the pin-hole collimator stationary during data acquisition or moving the pin-hole collimator during data acquisition.

14. The method of claim 8, further comprising placing the side detector less than approximately 50 degrees from normal to path x.

15. A Compton scatter subsystem for use in an X-ray computed tomography system having an energy source for directing energy along at least a path x toward an object which is located a distance from the energy source, wherein a portion of the energy from the energy source undergoes Compton effect upon interaction with the object to create a plurality of Compton scatter photons, wherein the system has a first detector a first distance from the object generally in-line of path x for detecting one or more types of radiation, the Compton scatter subsystem comprising:
- a side detector located a second distance from an object and generally normal to path x;
- a pin-hole collimator having at least one pin-hole, the pin-hole collimator located between the object and the side detector, wherein Compton scattering is measured for photons passing through the at least one pin-hole measured by the side detector; and
- wherein the system provides data related to interior features within the object, and obtains digital information on the object's 3-D geometry and properties.

16. The subsystem of claim 15, wherein the energy source is selected from a group consisting of an X-ray or gamma ray source.

17. The subsystem of claim 15, wherein the object is a human or a part of a human.

18. The subsystem of claim 15, wherein the side detector is stationary during data acquisition or is moved during data acquisition.

19. The subsystem of claim 15, wherein the pin-hole collimator is stationary during data acquisition or is moved during data acquisition.

20. The subsystem of claim 15, wherein the side detector is placed less than approximately 50 degrees from normal to path x.

21. An energy computed tomography system, comprising:
- an energy source for directing energy along at least a path x toward an object located a distance from the energy source, wherein a portion of the energy undergoes Compton effect upon interaction with the object to create a plurality of Compton scatter photons;
- a first detector positioned a first distance from the object generally in-line of path x for detecting one or more types of radiation;
- a Compton scattering subsystem located a second distance from the object generally normal to path x, the Compton scattering subsystem comprising:
  - a second detector; and
  - a pin-hole collimator located between the object and the second detector;
- wherein Compton scattering is measured for lower energy passing through the collimator measured by the second detector; and
- wherein the system provides data related to interior features within the object.

22. The system of claim 21, wherein the energy source is selected from the group consisting of X-ray and proton.

* * * * *